(12) United States Patent
Kostenich et al.

(10) Patent No.: US 8,768,425 B2
(45) Date of Patent: Jul. 1, 2014

(54) DEVICE AND METHOD FOR IDENTIFICATION OF MECONIUM IN AMNIOTIC FLUID

(75) Inventors: Genady Kostenich, Bat Yam (IL); Sol Kimel, Haifa (IL); Arie Orenstein, Tel Aviv (IL); Reuben Achiron, Tel Aviv (IL); Eliahu Pewzner, Modiin Ilit (IL)

(73) Assignee: Tel Hashomer Medical Research Infrastructure and Services Ltd., Ramat Gan (IL)

( * ) Notice: Subject to any disclaimer, the term of this patent is extended or adjusted under 35 U.S.C. 154(b) by 735 days.

(21) Appl. No.: 12/682,610

(22) PCT Filed: Oct. 5, 2008

(86) PCT No.: PCT/IL2008/001317
§ 371 (c)(1),
(2), (4) Date: Sep. 7, 2010

(87) PCT Pub. No.: WO2009/050693
PCT Pub. Date: Apr. 23, 2009

(65) Prior Publication Data
US 2010/0324391 A1    Dec. 23, 2010

Related U.S. Application Data

(60) Provisional application No. 60/960,845, filed on Oct. 16, 2007.

(51) Int. Cl.
*A61B 5/1455* (2006.01)
(52) U.S. Cl.
USPC .......................................... 600/342; 600/310

(58) Field of Classification Search
USPC ................................... 600/309–344
See application file for complete search history.

(56) References Cited

U.S. PATENT DOCUMENTS

| | | | | |
|---|---|---|---|---|
| 4,856,527 | A | * | 8/1989 | Karcher et al. ............... 600/342 |
| 4,922,919 | A | * | 5/1990 | Novack ......................... 600/320 |
| 5,172,693 | A | | 12/1992 | Doody |
| 5,361,759 | A | * | 11/1994 | Genevier et al. .............. 600/342 |
| 5,713,351 | A | * | 2/1998 | Billings et al. ................ 600/309 |
| 6,044,284 | A | * | 3/2000 | Eisenfeld et al. ............. 600/310 |
| 2004/0147843 | A1 | | 7/2004 | Bambot et al. |
| 2006/0241347 | A1 | | 10/2006 | Whitehead |

FOREIGN PATENT DOCUMENTS

| JP | 63-189125 | 8/1988 |
|---|---|---|
| WO | 92/00699 A | 1/1992 |

OTHER PUBLICATIONS

Kanayama et al., Determining Zinc Coproporphyrin in Maternal Plasma—A New Method for Diagnosing Amniotic Fluid Embolism, Clinical Chemistry, Apr. 1992, pp. 526-529, vol. 38, No. 4, XP002514187.

(Continued)

*Primary Examiner* — Eric Winakur
*Assistant Examiner* — Marjan Fardanesh
(74) *Attorney, Agent, or Firm* — Browdy and Neimark, PLLC (57) ABSTRACT

Disclosed are methods and devices comprising an elongated probe for the in vivo detection of meconium in amniotic fluid held in an amniotic sac based on detecting the presence of Zinc-coproporphyrin I (ZnCP). ZnCP is excited at approximately 405 nm and emits characteristic fluorescence, centered at about 580 nm and less intensely at 630 nm.

19 Claims, 6 Drawing Sheets

(56) References Cited

OTHER PUBLICATIONS

Naruse, et al., Study of the Specific Diagnosis of Meconium Aspiration Syndrome (MAS) with Fluorometry, Acta Abst Gynaec JPN, 1990, pp. 719-726, vol. 42, No. 7.
Anonymous, Ion laser, Wikipedia, the free encyclopedia, http://en.wikipedia.org/wiki/Argon_laser, Jan. 15, 2014, pp. 1-3.
Prahl, Optical Absorption of Hemoglobin, http://omlc.ogi.edu/spectra/hemoglobin/, Jan. 15, 2014, pp. 1-3.
Prahl, Tabulated Molar Extinction Coefficient for Hemoglobin in Water, http://omlc.ogi.edu/spectra/hemoglobin/summary.html, Jan. 15, 2014, pp. 1-6.

* cited by examiner

DEVICE AND METHOD FOR IDENTIFICATION OF MECONIUM IN AMNIOTIC FLUID

This is a U.S. National Phase Application of PCT Patent Application No. PCT/IL2008/001317, which was filed on 5 Oct. 2008, which claims the benefit of priority from U.S. Provisional Patent Application No. 60/960,845, which was filed on 16 Oct. 2007.

RELATED APPLICATION

This application claims the benefit under 119(e) of a U.S. provisional application with same title and inventors, filed on Oct. 16, 2007 and having Ser. No. 60/960,845, the disclosure of which is incorporated herein by reference.

FIELD AND BACKGROUND OF THE INVENTION

The present invention relates to the field of obstetrics and particularly to methods and devices useful in prenatal identification of meconium in amniotic fluid.

Amniotic fluid is a liquid that surrounds and protects the fetus inside the amniotic sac within the uterus.

During gestation, the colon of a fetus fills with meconium, fetal feces comprising bile and its metabolites, gastrointestinal and pancreatic secretions, mucus, cellular debris, swallowed vernix caseosa, lanuge, and blood. Usually, the fetus is continent until birth, but in a significant minority of births (7-22%) it is observed that the fetus has excreted a significant amount of meconium into the amniotic fluid leading to meconium-stained amniotic fluid (MSAF).

The pathophysiology of meconium excretion into the amniotic fluid is not entirely understood but it has been suggested that in some cases, the meconium excretion is caused by fetal distress due to, for example, acute or chronic fetal hypoxia.

Meconium present in the amniotic fluid apparently has a detrimental effect on the fetus, for example causing umbilical vessel constriction, vessel necrosis, and production of thrombi, potentially associated with ischemic cerebral palsy. Meconium alters the level of zinc in amniotic fluid, which may reduce the antibacterial properties of amniotic fluid, potentially facilitating intra-amniotic infection. Meconium has also been implicated as leading to other adverse effects, for example, increased preterm labor, altered coagulation profile in the fetus and neonatal seizures. Although the direct and indirect effects remain uncertain, MSAF is consistently identified as a predictor of maternal and perinatal complications with increased fetal risk, especially when fetal exposure time has been extended and the fluid is concentrated. It has been demonstrated that infants born in the presence of MSAF have lower overall infant assessment scores in comparison to newborns without meconium staining.

5-20% of infants born with meconium-stained amniotic fluid have meconium aspiration syndrome where meconeal particles enter the fetal lungs, leading to severe respiratory disorders. Infants with severe meconium aspiration syndrome develop pulmonary hypertension, progressive respiratory distress, hypoxia, hypercapnia, and acidosis. Infant mortality from meconium aspiration syndromes accounts for 2% of all perinatal deaths in developed countries.

A number of methods and devices are known for identifying the presence of meconium in amniotic fluid.

Amniocentesis is an invasive sampling technique which has become established in obstetric care for prenatal genetic testing (karyotyping).

In U.S. Pat. No. 5,361,759 is taught an invasive method for detection of meconium, blood or vernix in amniotic fluid by absorbance spectroscopy of a sample of amniotic fluid acquired by penetrating an amniotic sac.

In U.S. Pat. No. 5,713,351 is taught an invasive method for the detection of meconium or blood in amniotic fluid by penetrating an amniotic sac with a probe and withdrawing amniotic fluid through the lumen of the probe into an observation chamber.

In amnioscopy, a health-care professional directly observes the forebag of an amniotic sac through a dilated cervix to look for meconium staining. Although useful in identifying heavy staining, amnioscopy has not proven effective in identifying milder cases of staining. Amnioscopy requires an undesirable degree of cervical dilation.

In U.S. Pat. No. 5,172,693 is taught non-invasive detection of meconium in amniotic fluid held in an amniotic sac based on detecting fluorescence of the bilirubin component of meconium in meconium-stained amniotic fluid. A probe is placed against the body (preferably the uterine wall) and monochromatic excitation light at a wavelength of 488 nm or 514 nm (produced by an argon laser) is projected from the probe through the body tissue into the amniotic sac. If present in the amniotic fluid, bilirubin absorbs the excitation light and emits characteristic fluorescence.

It would be highly advantageous to have a method for detecting the presence of meconium in amniotic fluid having advantages over the methods known in the art.

SUMMARY OF THE INVENTION

The present invention provides methods and devices for the identification of meconium, for example in meconium-stained amniotic fluid. In some embodiments, excitation light including light having a wavelength of approximately 405 nm is projected through the walls of an amniotic sac, preferably an intact amniotic sac. If meconium is present in the amniotic fluid, the zinc coproporphyrin I (ZnCP) component of the meconium absorbs the excitation light and emits light having a characteristic wavelength, for example at 580 nm and/or 630 nm, by fluorescence. Embodiments of the present invention are sensitive and accurate at identifying even low concentrations of meconium in amniotic fluid, allowing early identification of meconium-stained amniotic fluid. Early identification of meconium-stained amniotic fluid may allow a health-care professional to take steps to avoid at least some of the negative effects of meconium-stained amniotic fluid, for example minimizing the incidence of meconium aspiration syndrome and/or decreasing the need for neonatal intensive care and/or decreasing associated deaths as a result of exposure of a fetus to meconium.

Thus according to some embodiments of the teachings of the present invention there is provided, a method for identifying the presence of meconium in amniotic fluid, comprising: a) providing an excitation unit configured to provide excitation light including a wavelength of about 405 nm; b) illuminating amniotic fluid through the wall of an amniotic sac (in some embodiments without penetrating the amniotic sac) with the excitation light in order to excite Zinc-coproporphyrin I (ZnCP) present in the amniotic fluid; c) subsequent to b, monitoring the amniotic fluid for emission of light, indicative of the presence of ZnCP, resulting from excitation by the excitation light; and d) upon detection of substantial emission of the light indicative of the presence of ZnCP, identifying the presence of meconium in the amniotic fluid.

In embodiments, the concentration of ZnCP in the amniotic fluid is quantified. In embodiments, the concentration of ZnCP quantified in the amniotic fluid is rated as a qualitative degree of meconium in the amniotic fluid, e.g. "clear", "low", "medium" or "thick".

In some embodiments, the excitation light is collimated.

In some embodiments, the excitation unit comprises an excitation light source for generating the excitation light.

In some embodiments, the excitation light consists essentially of monochromatic light of about 405 nm.

In some embodiments, the method further comprises, prior to the illumination of the amniotic fluid with the excitation light, passing a portion of the excitation unit into and/or through the cervix, for example to provide a direct line of sight to an outer surface of the amniotic sac. In some embodiments, the portion of the excitation unit passed into and/or through the cervix is a distal tip of a probe, the probe including an excitation light guide.

In some embodiments, the passing of the portion of the illumination unit into and/or through the cervix is guided with the help of an imaging modality. In some embodiments, the method of the present invention further comprises providing an imaging unit configured to generate an image from radiation entering the probe. In some embodiments the radiation is light and, preferably, the method further comprises illuminating the cervix with light to allow production of an image useful in guiding the probe.

In some embodiments, the portion of the excitation unit is placed through the external os and in the endocervical canal. In some embodiments, the portion of the excitation unit is placed past the internal os of endocervical canal. In some embodiments, the portion of the excitation unit is placed inside the uterine volume.

In some embodiments, the method further comprises, prior to the illuminating of the amniotic fluid with the excitation light, contacting a portion of the illumination unit with the outer surface of the amniotic sac. In some embodiments, the contacting of a portion of the illumination unit (e.g., the distal end of a probe) with the outer surface of the amniotic sac is monitored with the help of an imaging modality, that is to say, the imaging modality is used to ensure that the portion of the illumination unit is not pushed too far so as to penetrate or otherwise substantially damage the amniotic sac. For example, in some embodiments, after the portion of the illumination unit has been placed in the external os of the cervix and is pushed forward through the endocervical canal (towards the internal os, internal volume of the uterus and outer surface of the amniotic sac) an intensity of light (for example of excitation light) projected from and reflected back to the contacting portion of the illumination unit is monitored. In such a way, pushing of the portion of the illumination unit is stopped when the intensity of reflected light indicates that the amniotic sac has been contacted.

In some embodiments, monitoring the amniotic fluid for emission of light indicative of the presence of ZnCP comprises guiding light from the amniotic fluid through a detection light guide of the probe.

In some embodiments, the indicative light comprises a wavelength of about 580 nm and/or about 630 nm, emitted by a fluorescence process by ZnCP present in the amniotic fluid as resulting from the illumination of the ZnCP by the excitation light.

In some embodiments, monitoring of emission of light indicative of the presence of ZnCP comprises comparing a detected intensity of light of about 580 nm ($I_{580}$) with the intensity of light comprising wavelengths significantly shorter ($I_{short}$) than 580 nm, e.g., at least about 5 nm and even at least about 10 nm shorter and/or significantly longer $I_{long}$) than 580 nm e.g., at least about 5 nm and even at least about 10 nm longer than 580 nm.

According to some embodiments of the present invention there is also provided a device useful for in vivo identification of the presence of meconium in amniotic fluid, comprising: a) an excitation unit configured to illuminate in vivo amniotic fluid past the cervix and through a wall of an amniotic sac with excitation light including a wavelength of about 405 nm; and b) a detection unit configured to detect an intensity of light indicative of the presence of ZnCP emitted from in vivo amniotic fluid.

In some embodiments, the illumination unit includes an excitation light source configured to produce light including a wavelength of about 405 nm.

In some embodiments, the device is configured to produce collimated excitation light.

In some embodiments, the device is configured to produce excitation light that consists essentially of monochromatic light of about 405 nm.

In some embodiments, the detection unit is configured to detect the intensity of emitted light passing through a wall of an amniotic sac. In some embodiments, the detection unit is configured to detect the intensity of emitted light passing through a wall of an amniotic sac towards the internal os of the endocervical canal. In some embodiments, the detection unit is configured to detect the intensity of emitted light passing through a wall of an amniotic sac and entering, at least partially, the endocervical canal. In some embodiments, the detection unit is configured to detect the intensity of emitted light passing through a wall of an amniotic sac and exiting the endocervical canal.

In some embodiments, the emitted light indicative of the presence of ZnCP has a wavelength about 580 nm and/or about 630 nm.

In some embodiments, the detection unit is configured to detect an intensity of emitted light indicative of the presence of ZnCP, e.g., about 580 nm ($I_{580}$) and/or about 630 nm ($I_{630}$), an intensity of light comprising wavelengths significantly shorter ($I_{short}$), e.g., at least about 5 nm and even at least about 10 nm shorter and/or significantly longer ($I_{long}$) than of the indicative light e.g., at least about 5 nm and even at least about 10 nm longer than 580 nm.

In some embodiments, the device further comprises at least one elongated probe having a distal end and a proximal end, including an excitation light guide component of the excitation unit, the excitation light guide having a distal end, a distal tip and a proximal end, the excitation light guide configured to guide the excitation light from the light source out through the distal tip of the excitation light guide.

In some embodiments the distal end of the probe is thin, preferably having a diameter of no more than about 6 mm (18 French) and even no more than about 4 mm (12 French). In some embodiments the distal end of a probe is significantly thinner, for example having a diameter of no more than about 3 mm (10 French), no more than about 2 mm (6 French) and even no more than about 1 mm (3 French).

In some embodiments, the distal end of the probe is configured to pass into and/or through a cervix, for example to provide the distal tip of the light guide with a direct line of sight with an outer surface of the amniotic sac. In some embodiments, the distal tip of the elongated probe is configured to contact the outer surface of an amniotic sac. In some embodiments, the distal tip of the light guide is configured to contact the outer surface of an amniotic sac.

In some embodiments, the probe includes a detection light guide component of the detection unit configured to guide light from a distal tip of the probe to a light detector component of the detection unit. In some embodiments, the detection light guide and the excitation light guide are discrete. In some embodiments, the detection light guide and the excitation light guide are substantially the same. An advantage of embodiments where the detection light guide and the excitation light guide are substantially the same is that the single component (e.g., a single optical fiber or bundle of optical fibers) used as the detection light guide and excitation light guide has a diameter that makes up a relatively large proportion of the area of the tip of the probe. Such a probe can then be designed to be relatively narrow (in order to reduce discomfort and other ill effects when passed into or through a cervix) and yet the detection light guide is large enough to collect sufficient emitted light to ensure high sensitivity.

In some embodiments, the device is configured to detect the intensity of reflected excitation light, for example to determine the proximity of the distal tip of the probe to the outer surface of the amniotic sac.

In some embodiments, the device further comprises an imaging unit, configured to generate a viewable image of the vicinity of the distal end of the probe. In some embodiments, the imaging unit is further configured to display a viewable image from light captured at the distal end of the probe. In some embodiments, the probe includes an image-acquisition light guide component of the imaging unit configured to guide light from the distal tip of the probe to an image processor of the imaging unit. In some embodiments, the image-acquisition light guide and the excitation light guide are discrete. In some embodiments, the image-acquisition light guide and the excitation light guide are substantially the same.

In some embodiments, the device further comprises an illumination light source, configured to illuminate the vicinity of the distal tip of the probe, e.g., to allow an imaging unit to acquire images of the vicinity of the distal tip of the probe. In some embodiments, the probe includes an illumination light guide configured to guide light from an illumination light source to the distal end of the probe. In some embodiments, the illumination light guide and the excitation light guide are discrete. In some embodiments, the illumination light guide and the excitation light guide are substantially the same. In some embodiments, the illumination light source and the excitation light source are discrete. In some embodiments, the illumination light source and the excitation light source are substantially the same.

In some embodiments, the device comprises a device body containing the excitation light source wherein a proximal end of the probe is configured to reversibly couple to the device body so that when the probe is coupled to the device body, the probe is configured to direct excitation light from the proximal end of the excitation light guide out through the distal tip of the excitation light guide.

In some embodiments, the at least one probe is sterile and packaged in a sterility preserving package.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of".

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

As used herein, the indefinite articles "a" and "an" mean "at least one" or "one or more".

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF EMBODIMENTS

The present invention relates to methods and devices for identifying the presence of meconium in amniotic fluid by exciting meconium components and detecting the light subsequently emitted by fluorescent processes.

Some embodiments of the present invention allow for the safe identification of meconium in amniotic fluid with high sensitivity.

Specifically, some embodiments of the present invention provide methods and devices for the identification of meconium in utero, for example in meconium-stained amniotic fluid. In some embodiments, excitation light including light having a wavelength of approximately 405 nm is projected through the wall of an intact amniotic sac. If meconium is present in the amniotic fluid, the zinc coproporphyrin I (ZnCP) component of the meconium absorbs the excitation light and emits characteristic fluorescence, centered at about 580 nm (narrow peak) and less intensely centered at about 630 nm (broader peak).

It has been found that illuminating amniotic fluid at about 405 nm for the identification of meconium provides many potential advantages that, in some embodiments of the invention, are utilized.

A first advantage is that despite the fact that meconium is a complex mixture of many different materials, many of which are fluorescent, the emission spectrum produced when meconium is excited with light having a wavelength of about 405 nm is relatively simple, having an intense and relatively narrow emission centered around 580 nm and a less intense and somewhat broader emission at about 630 nm. In some embodiments, the narrowness of the 580 nm emission is utilized to simplify determination whether detected light is an artifact, for example corresponding to random noise, or identification of meconium in amniotic fluid.

A second advantage is that the 405 nm excitation light is efficiently absorbed by blood. Thus, excitation light accidentally projected at the eyes of a fetus is absorbed by the eyelids and causes no damage. This allows, in some embodiments, the use of relatively intense excitation light allowing increased sensitivity, detection of low concentrations of meconium and earlier identification of potential problems. Further, the fact that 405 nm excitation light is efficiently absorbed by blood means that little, if any, excitation light is reflected inside the body.

A third advantage is that the 580 nm emitted light is efficiently absorbed by blood but passes substantially unattenuated through the amniotic sac. Thus, substantially any light having a wavelength of 580 nm detected through the wall of an amniotic sac is light emitted by fluorescent processes of ZnCP excited by excitation light and is not light that has entered from outside the body. This fact allows for the use of extremely sensitive detectors such as photomultiplier tubes. The use of extremely sensitive detectors in turn allows the collection of emitted light to be sub-optimal or less efficient. For example, relatively narrow light guides which cause less discomfort and have fewer potential adverse effects when passed into or through a cervix may be used both for illuminating amniotic fluid (less excitation light is needed) and for detection (collection of emitted light may be less efficient). For example, instead of the more efficient silicon glass optical fiber guides, in embodiments the present invention may be implemented using less efficient polymer optical guides. Polymer optical fibers are generally more flexible than silicon glass optical fibers allowing for greater ease of use. Polymer optical fibers are also generally cheaper than silicon glass optical fibers so one can more easily countenance producing one-use or disposable probes.

A fourth advantage is that the 405 nm excitation light as well as the 580 nm emitted light pass through the wall of the amniotic sac allowing application of the present invention without physically penetrating the amniotic sac by projecting the excitation light through the wall of the amniotic sac and detecting light that passes back through the wall of the amniotic sac. In some embodiments, the excitation light is projected through the cervix. In some embodiments, a probe is pushed into or through the cervix and excitation light projected through the end of the probe.

A fifth advantage is that light emission at about 580 nm and/or about 630 nm, upon excitation at about 405 nm, is apparently due to ZnCP, a material that is highly soluble in amniotic fluid. The high solubility means that the ZnCP is evenly distributed in the amniotic fluid (and not concentrated in a specific region) increasing the chance that meconium-stained amniotic fluid will be detected.

A sixth advantage is that, in embodiments as demonstrated herein, the excitation of ZnCP in amniotic fluid with 405 nm excitation light and detection of light emitted by fluorescent processes allows for quantification of the amount of ZnCP and correlation of the amount of ZnCP and the degree of meconium staining of the amniotic fluid.

An embodiment of the method of the present invention will be discussed as implemented with a device 10 of the present invention depicted in FIGS. 1A, 1B and 2.

Figure 1A:
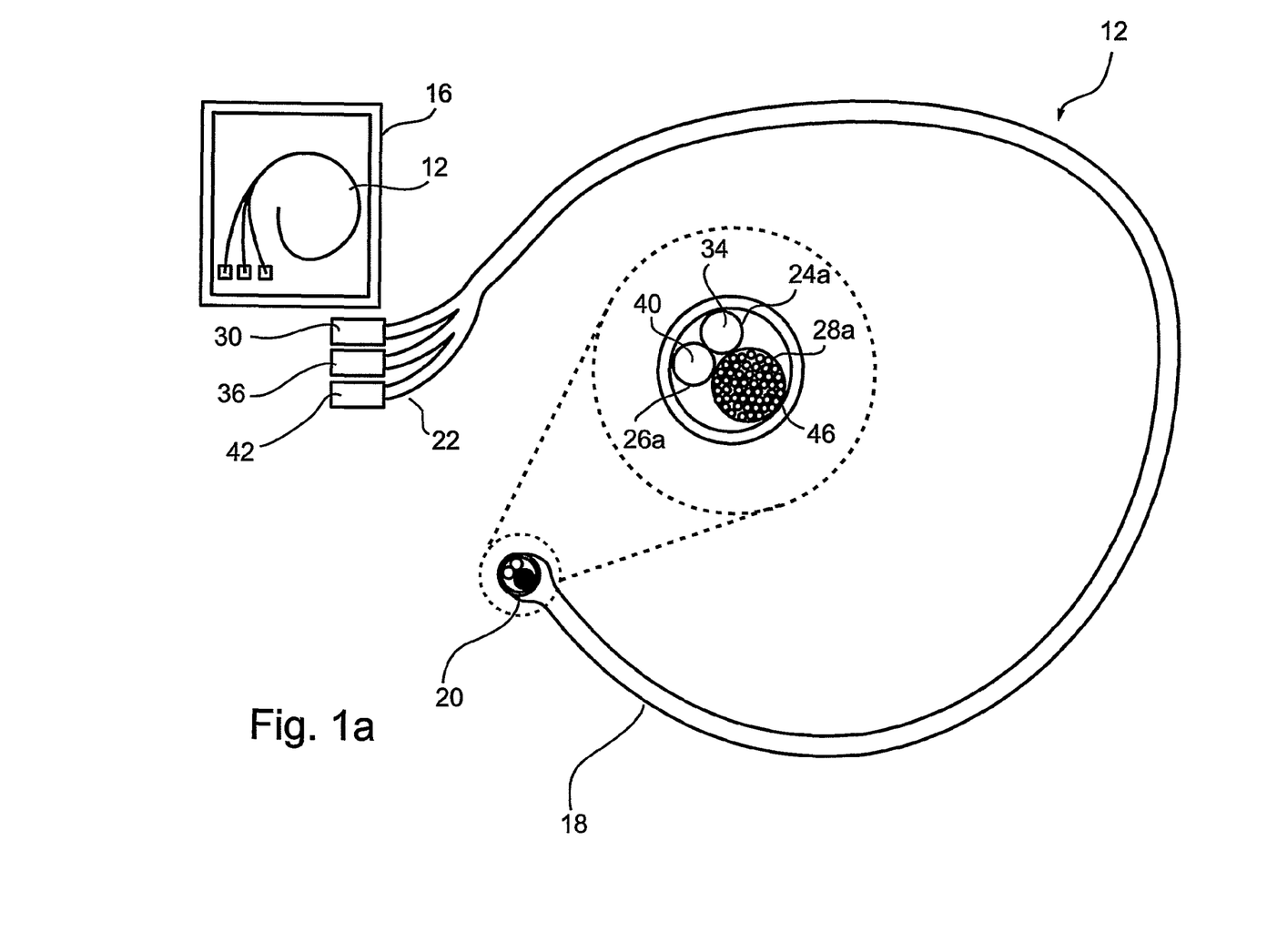
FIGS. 1a and 1b depict an embodiment of a device of the present invention.
Figure 1B:
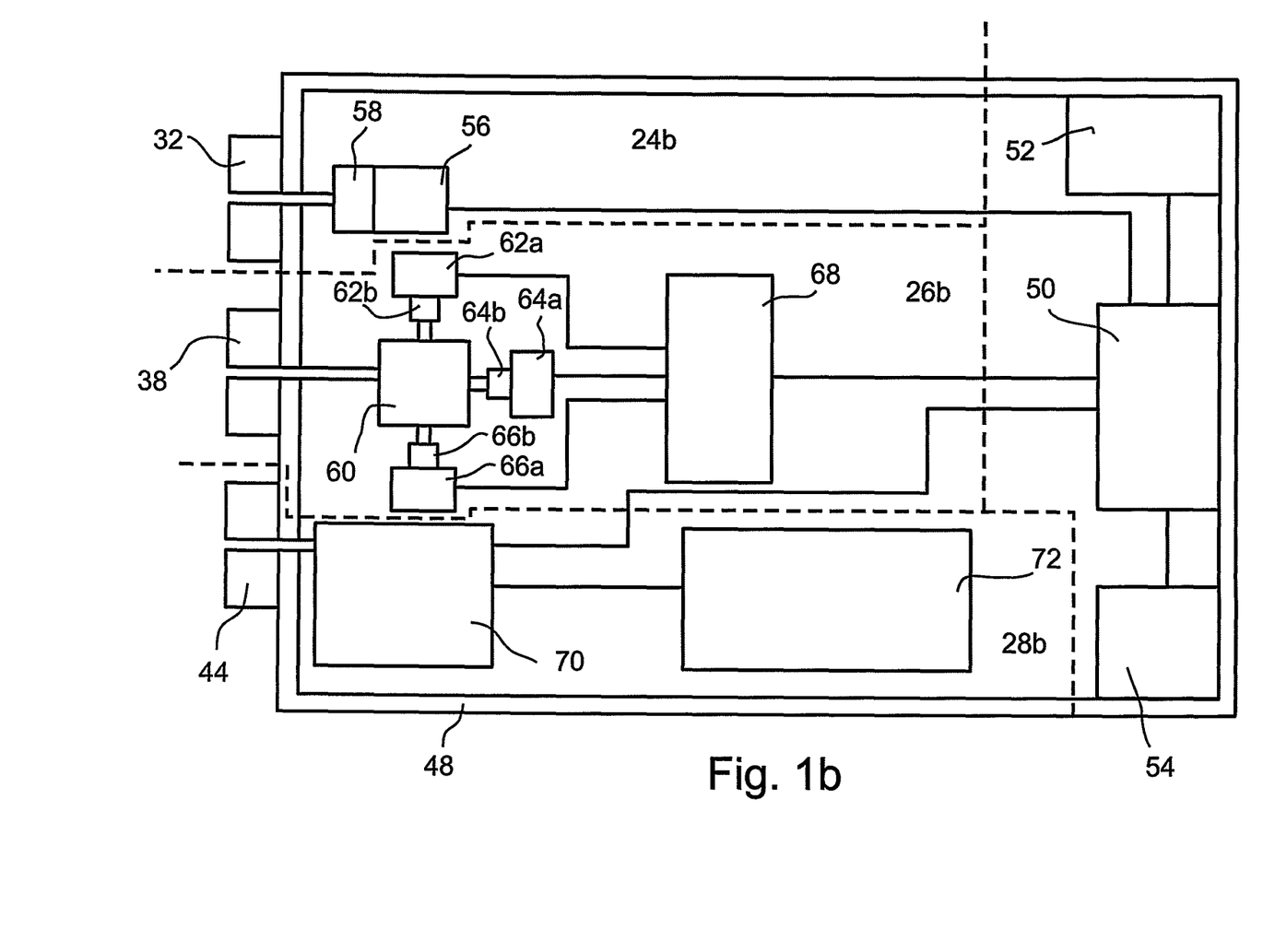
Figure 2:
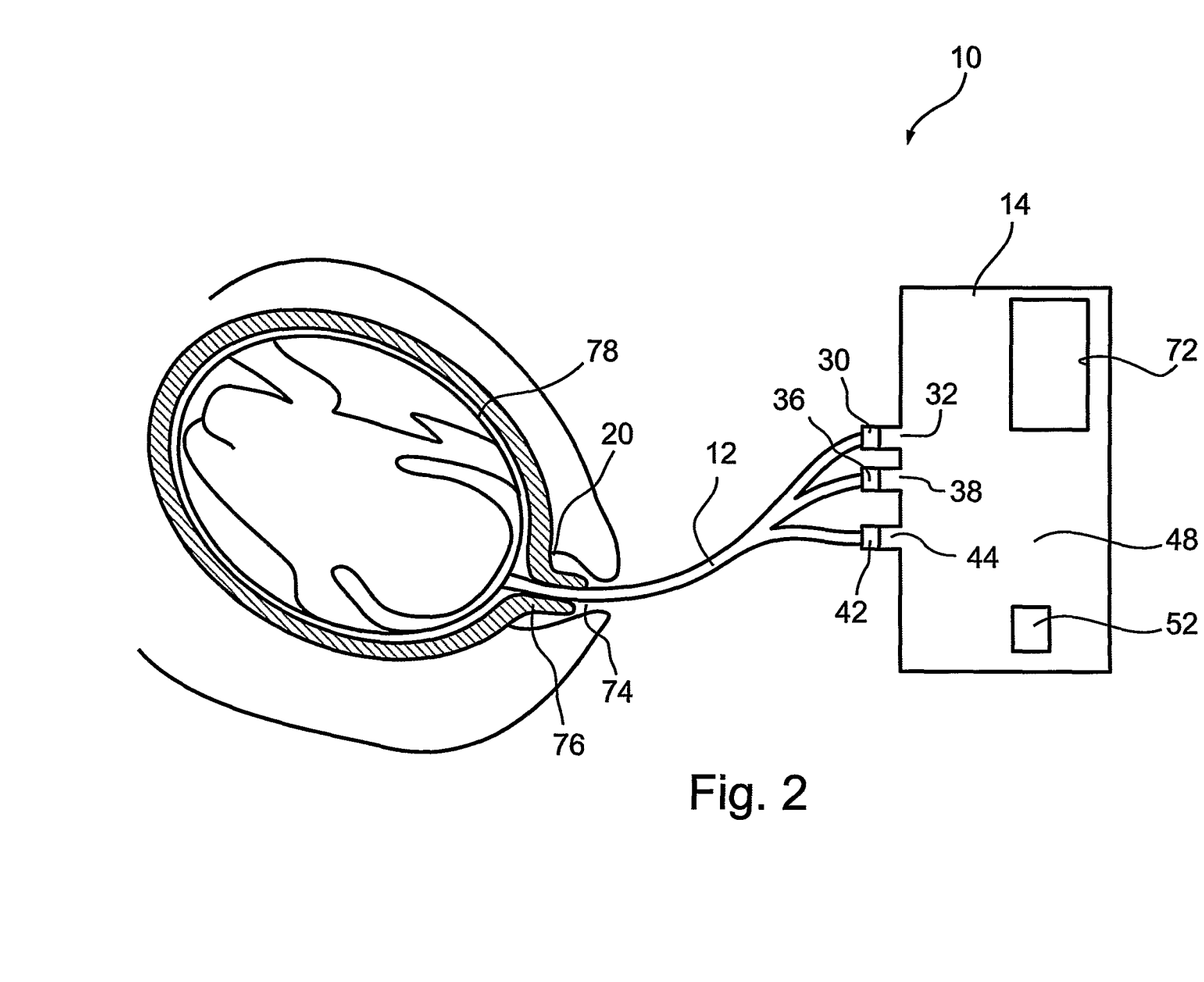
FIG. 2 is a depiction of the device of FIGS. 1 in use for implementing an embodiment of the method of the present invention.

Device 10 comprises a plurality of elongated probes 12 (FIG. 1A) and a device body 14 (FIG. 1B) where a probe 12 is configured to couple to device body 14 (FIG. 2).

Probes 12 are substantially thin, flexible catheters (such as urological catheters) comprising a plurality of light guides. Each of probes 12 is configured for one-time use, that is to say, disposable after use. Each probe 12 is sterile (sterilized, for example with ethylene oxide or gamma radiation) and individually packaged in a sterility preserving package 16.

In FIG. 1A is depicted an individual probe 12. Probe 12 has a distal end 18, a distal tip 20 and a trifurcated proximal end 22 and comprises three separate optical fiber light guides: excitation/illumination light guide 24a, detection light guide 26a and image-acquisition light guide 28a. Distal end 18 of probe 12 is substantially a 1 mm (3 French) outer diameter silicone rubber catheter that is configured to pass through a cervix.

Excitation/illumination light guide 24a (e.g., a 250 micrometer diameter polymer optical fiber) passes from distal end 18 of probe 12 to the branch of proximal end 22 of probe 12 that ends with excitation/illumination probe coupling adaptor 30 configured to reversibly couple to an excitation/light body coupling adaptor 32 of device body 14. Excitation/illumination light guide 24a is a component of an excitation/illumination unit 24 of device 10. When properly coupled to device body 14, excitation/illumination light guide 24a directs light from components 24b of excitation/illumination unit 24 in device body 14 out through distal tip 34 of excitation/illumination light guide 24a.

Detection light guide 26a (e.g., a 250 micrometer diameter polymer optical fiber) passes from distal end 18 of probe 12 to the branch of proximal end 22 of probe 12 that ends with detection probe coupling adaptor 36 configured to reversibly couple to a detection body coupling adaptor 38 of device body 14. Detection light guide 26a is a component of a detection unit 26 of device 10. When properly coupled to device body 14, detection light guide 26a guides light from distal tip 40 of detection light guide 26a to a light detector component 26b of detection unit 26 in device body 14.

Image-acquisition light guide 28a (in device 10 comprising polymer optical fibers, specifically a leached fiber optic image bundle, 0.67 mm outer diameter of 8.9 micrometer diameter clad glass fibers available from Schott AG, Mainz, Germany) passes from distal end 18 of probe 12 to the branch of proximal end 22 of probe 12 that ends with image-acquisition probe coupling adaptor 42 configured to reversibly couple to an image-acquisition body coupling adaptor 44 of device body 14. Image-acquisition light guide 28a is a component of an image-acquisition unit 28 of device 10. When properly coupled to device body 14, image-acquisition light guide 28a guides light from distal tip 46 of image-acquisition light guide 28a to components 28b of image-processing unit 28 in device body 14.

Distal tips 34, 40 and 46 of excitation/illumination light guide 24a, detection light guide 26a and image-acquisition light guide 28a respectively are all flush with distal tip 20 of probe 12.

Device body 14, schematically depicted in FIG. 1B, comprises a casing 48 which contains other components of device 10 including: components 24b of excitation/illumination unit 24 which are functionally associated with excitation/illumination body coupling adaptor 32; components 26b of detection unit 26 which are functionally associated with detection body coupling adaptor 38; components 28b of image-processing unit 28 which are functionally associated with image-acquisition body coupling adaptor 44; a processing unit 50; a results display unit 52 and a power supply 54.

Components 24b of excitation/illumination unit 24 contained within casing 48 include an excitation/illumination light source 56 (a light-emitting diode) configured to provide substantially monochromatic light with a wavelength of 405 nm and a collimator 58. When activated, light source 56 provides light that passes through collimator 58 which is directed towards to excitation/illumination body coupling adaptor 32.

Components 26b of detection unit 26 contained within casing 48 include a beam splitter 60 to split a beam of light entering from detection body coupling adaptor 38 to three parts and direct each of the three parts to a different light detector (e.g., a photomultiplier tube or a diode) 62a, 64a or 66a through a different filter 62b 64b, 66b, respectively. Each filter is configured to allow passage of light having a narrow range of wavelengths: 62b only about 570 nm; 64b only about 580 nm; and 66b only about 590 nm. Each light detector 62a, 64a or 66a is configured to measure and report an intensity of light impinging on the detector to an analogue to digital converter 68 functionally associated with processing unit 50.

Imaging unit 28 of device 10 is configured to generate and display a viewable image of the vicinity of distal end 18 of probe 12. Components 28b of imaging unit 28 receive light through from image-acquisition body coupling adaptor 44, where image-processor 70 converts the received light to a visible image that is displayed on image display unit 72.

Controller unit 50 is functionally associated with other components of device 10 to act as a processor, controller and configured to allow user input to device 10. Particularly, controller unit 50 receives the intensities of light measured by light detectors 62a, 64a and 66a to determine if meconium is identified in amniotic fluid, as discussed below.

Power supply 54 is a standard rechargeable battery (e.g., Li-ion battery) configured to provide power to the other components of device 10.

An embodiment of the method of the present invention is depicted with reference to device 10, FIGS. 1A and 1B as well as FIG. 2.

For use, a probe 12 is removed from a respective sterility preserving package 16. Probe coupling adaptors 30, 36 and 42 at proximal end 22 of probe 12 are coupled to body coupling adaptors 32, 38 and 44, respectively, of device body 14. As a result, components 24b of excitation/illumination unit 24 are functionally associated with excitation/illumination light guide 24a so that light provided by light source 56 is directed from the proximal end of excitation/illumination light guide 24a out through distal tip 34 of light guide 24a. Components 26b of detection unit 26 are functionally associated with detection light guide 26a so that detection light guide 26a guides light from distal tip 40 to components 26b such as detectors 62a, 64a and 66a. Further, image-acquisition light guide 28a is functionally associated with imaging unit 28 so that image-acquisition light guide 28a guides light from distal tip 46 of image-acquisition light guide to other components of imaging unit 28.

Using controller unit 50, a user activates excitation/illumination light source 56, detectors 62a, 64a and 66a and imaging unit 28.

The user places distal end 18 of probe 12 into a vagina 74. Light from excitation/illumination light source 56 illuminates the inside of vagina 74 and is directed back through image-acquisition light guide 28a to imaging unit 28 which generates and displays a viewable image of the inside of vagina 74 on image-displaying unit 72. With the assistance of the displayed image, the user directs distal end 18 of probe 12 into and through cervix 76 so as to provide distal tip 40 of detection light guide 26a with a direct line of sight with an outer surface of amniotic sac 78. Distal tip 20 of probe 12 is pushed against the outer surface of amniotic sac 78, as depicted in FIG. 2.

In such a position, amniotic fluid in amniotic sac 78 is illuminated through the wall of amniotic sac 78, without penetrating the wall, with the 405 nm wavelength excitation light provided by excitation/illumination light source 56. If meconium is present in the amniotic fluid, the ZnCP component of the meconium absorbs the excitation light and emits light by fluorescent processes, including at 580 nm.

Detection unit 26 continuously monitors the emitted light, that is to say light emitted by the amniotic fluid enters distal tip 40 of detection light guide 26a and is guided to components 26b of detection unit 26.

A third of the light is directed by beam splitter 60 through filter 62b to detector 62a. As filter 62b allows only light with a wavelength of about 570 nm to pass, detector 62a detects an intensity of emitted light with a wavelength of 570 nm, $I_{570}$.

A third of the light is directed by beam splitter 60 through filter 64b to detector 64a. As filter 64b allows only light with a wavelength of about 580 nm to pass, detector 64a detects an intensity of emitted light with a wavelength of 580 nm, $I_{580}$, corresponding to light emitted by ZnCP upon excitation with 405 nm light, and thus indicative of the presence of ZnCP.

A third of the light is directed by beam splitter 60 through filter 66b to detector 66a. As filter 66b allows only light with a wavelength of about 590 nm to pass, detector 66a detects an intensity of emitted light with a wavelength of 590 nm, $I_{590}$.

Controller unit 50 receives $I_{570}$, $I_{580}$ and $I_{590}$ and compares whether or not $I_{580}$ is significantly higher than $I_{570}$ and $I_{590}$, indicating that ZnCP is present in the amniotic fluid, for example by comparing if $2 \times (I_{580})/(I_{570}+I_{590})$ is greater than 1: if the result is greater than 1, then the presence of meconium in the amniotic fluid is identified. If controller unit 50 identifies the presence of meconium in the amniotic fluid, this fact is displayed on results display unit 52.

Subsequent to examination, probe 12 is withdrawn from cervix 76 and vagina 74, probe coupling adaptors 30, 36 and 42 decoupled from respective body coupling adaptors 32, 38 and 44, and probe 12 discarded.

In the embodiment of the method of the present invention described above, a portion of excitation unit 24 (distal tip 34 of excitation/illumination light guide 24a) is pushed into and through cervix 76 to contact the outer surface of amniotic sac 78. In some embodiments, a portion of an excitation unit is pushed into and through a cervix to provide a line of sight to an outer surface of an amniotic sac, without necessarily contacting the amniotic sac. In some embodiments, a portion of an excitation unit is pushed into a cervix to provide a line of sight to an outer surface of an amniotic sac, without necessarily contacting the amniotic sac. In some embodiments, a portion of an excitation unit is located so as to illuminate the amniotic fluid with excitation light that passes through the cervix (e.g., through a mucosal plug in the cervix) without entering or passing through the cervix.

In the embodiment of the method of the present invention described above, detection of substantial emission of light indicative of the presence of ZnCP is determined by comparing the intensity of light gathered by detection light guide 26a having an indicative wavelength ($I_{580}$) with the intensity of light at two reference wavelengths, one shorter ($I_{570}$) and one longer ($I_{590}$) than the indicative wavelength. One skilled in the art is able to formulate and implement other suitable measurements and methods to determine whether or not there is substantial emission of light indicative of ZnCP.

Distal end 18 of probe 12 of device 10 described above has an external diameter of 1 mm (3 French). It is preferable that a distal end of a probe of a device of the present invention that is configured to pass through a cervix be as small as possible to cause as little discomfort as possible, e.g., having an outer diameter of less than about 6 mm and even less than about 4 mm (12 French). In embodiments the distal end of a probe is significantly thinner, for example having a diameter of no more than about 3 mm (10 French), no more than about 2 mm (6 French) and even no more than about 1 mm (3 French).

Probe 12 of device 10 is substantially a cervical catheter including three distinct light guides: excitation/illumination light guide 24a, detection light guide 26a and image-acquisition light guide 28a. In some embodiments, a probe includes a lesser or greater number of light guides. For example, in some embodiments, the excitation light guide and the illumination light guide are discrete, while in some embodiments such as probe 12 of device 10, the excitation light guide and the detection light guide are the same light guide 24a. For example, in some embodiments, the excitation light guide and the detection light guide are substantially the same, while in some embodiments such as probe 12 of device 10, excitation light guide 24a and the detection light guide 26a are discrete. For example, in some embodiments, the excitation light guide and the image-acquisition light guide are substantially the same, while in some embodiments such as probe 12 of device 10, excitation light guide 24a and the image-acquisition light guide 28a are discrete. In some embodiments, the illumination light guide and the image-acquisition light guide are substantially the same, while in some embodiments such as probe 12 of device 10, illumination light guide 24a and the image-acquisition light guide 28a are discrete. In some embodiments, the illumination light guide and the detection light guide are substantially the same, while in some embodiments such as probe 12 of device 10; illumination light guide 24a and detection light guide 26a are discrete. In some embodiments, the image-acquisition light guide and the detection light guide are substantially the same, while in some embodiments such as probe 12 of device 10, image-acquisition light guide 28a and detection light guide 26a are discrete.

In probe 12 of device 10, distal tips 34, 40 and 46 of excitation/illumination light guide 24a, detection light guide 26a and image-acquisition light guide 28a respectively are all flush with distal tip 20 of probe 12. In some embodiments, one or more light guides are not flush with a distal tip of a respective probe.

Light guides 24a, 26a and 28a of probe 12 consist essentially of bundles of polymer optical fibers, which are relatively cheap and easy to use in the manufacture of a probe such as 12. Suitable polymer optical fiber bundles include "POF Image Guides" commercially available from Industrial Fiber Optics (Tempe, Ariz., USA) which are flexible solid rods made up of thousands of individual plastic fibers, bonded as a single coherent fiber bundle so that all images transferred from one end of the bundle to the other end retain their original spatial properties.

In some embodiments, the fibers are acrylic fibers that have reasonable optical transmission capability, are relatively flexible but are also relatively expensive.

In some embodiments, the fibers are polystyrene fibers so are cheaper but have a lower optical transmission ability. However, in such embodiments the lower optical transmission is adequate, as discussed above.

In some embodiments optical fibers made of other materials, for example silicon glass or sapphire, are used as light guides for implementing the teachings of the present invention. In some embodiments, other types of light guides are used.

The distal tip of a probe, e.g. tip 20 of probe 12, is preferably not sharp in order to avoid damage to tissue during use. In embodiments, a spherical lens is located at the end of a distal end of a probe, both to protect against tissue damage and to enhance the optical properties of the probe.

Probe 12 of device 10 described above is configured to be disposable after one use. As discussed above, a plurality of sterile probes 12, individually packaged in sterility preserving packages 16, may be provided to a user. In some embodiments, probes are not necessarily configured for disposal after one use. In some embodiments such probes are not sterile and are used as-is or the distal end of a probe is sterilized before use, for example by dipping in boiling water or contacting with a disinfectant or antiseptic such as a solution including isobutanol, ethanol and/or chlorhexidine gluconate. In some embodiments the distal end of a probe is covered with a disposable sheath that is substantially transparent to the excitation and emission wavelengths, for example of latex, before use.

In device 10 a single physical unit 24 functions both as an excitation unit to provide and direct excitation light at amniotic fluid and as an illumination unit to illuminate the region proximal to a distal tip 20 of a probe 12 to assist in guiding distal end 18 of probe 12 to vicinity of a cervix. In some embodiments, a device of the present invention is provided with an illumination unit that includes at least one, and in some embodiments, substantially all components that are distinct from an excitation unit.

Device 10 described above is provided with an excitation/illumination unit 24 comprising a light source 56, a light-emitting diode configured to provide monochromatic light having a wavelength of 405 nm and is provided with a collimator 58 to collimate the provided light. In some embodiments, the teachings of the present invention are implemented with other suitable types of excitation and/or illumination light sources, for example, continuous light sources, variable light sources, lasers, incandescent light sources, fluorescent light sources, arc lamps or any other suitable light source. In some embodiments, light emitting diodes are preferred as these are cheap and economical in energy use, in some instances allowing such a device to be small and hand-held. In some embodiments, the excitation light provided by an illumination unit is not collimated.

Device 10 described above is provided with an integral imaging unit 28 that generates images with the help of light provided by excitation/illumination light source 56, which also functions as an excitation light source. In some embodiments, a device of the present invention is provided with a dedicated illumination light source, for example an illumination light source producing white light.

Device 10 described above is provided with an integral imaging unit 28 comprising image processor 70, illumination light guide 24a and image-acquisition light guide 28a to assist in guiding distal end 18 of probe 12 to a location suitable for identifying meconium in amniotic fluid in an amniotic sac. In some embodiments, a device of the present is devoid of an integral imaging system and a probe is guided to a suitable location with an external imaging system, for example a standard ultrasound imaging device that is often found in gynecological clinics, e.g., Mindray DP-6600 (National Ultrasound, Duluth, Ga., USA). In some embodiments, a probe is guided to a suitable location by touch without an imaging system, for example when the user of the device is an exceptionally skilled gynecologist, obstetrician or midwife.

Device 10 described above is provided with a detection unit 26 configured to detect the intensity of emitted light at three distinct wavelengths, the intensity at the wavelength indicative of the presence of ZnCP ($I_{580}$) and the intensities at two reference wavelengths, (e.g., $I_{570}$ and $I_{590}$ as discussed above or $I_{560}$ and $I_{600}$ as discussed below). For example, in some embodiments, other suitable configurations of a detection unit are used. For example, in some embodiments, the intensity at an indicative wavelength different from 580 nm is measured. For example, in some embodiments, the intensity at more than one indicative wavelength is measured. For example, in some embodiments, the intensity at none, one or more than two reference wavelengths is measured.

Device 10 described above is provided with a controller unit 50 functionally associated with a results display unit 52, allowing device 10 to be a portable device used independently of other devices. In some embodiments, some or all of the functions performed by controller unit 50 are performed by another device, for example a computer. In some embodiments, a device of the present invention is devoid of a results display unit and results are displayed otherwise.

Device 10 described above is provided with a rechargeable battery contained within casing 48 as a power supply 54. In some embodiments, a device of the present invention is provided with any other suitable power supply. For example, in some embodiments, power is supplied from an external source, for example with the help of a cable (see below).

Figure 3:
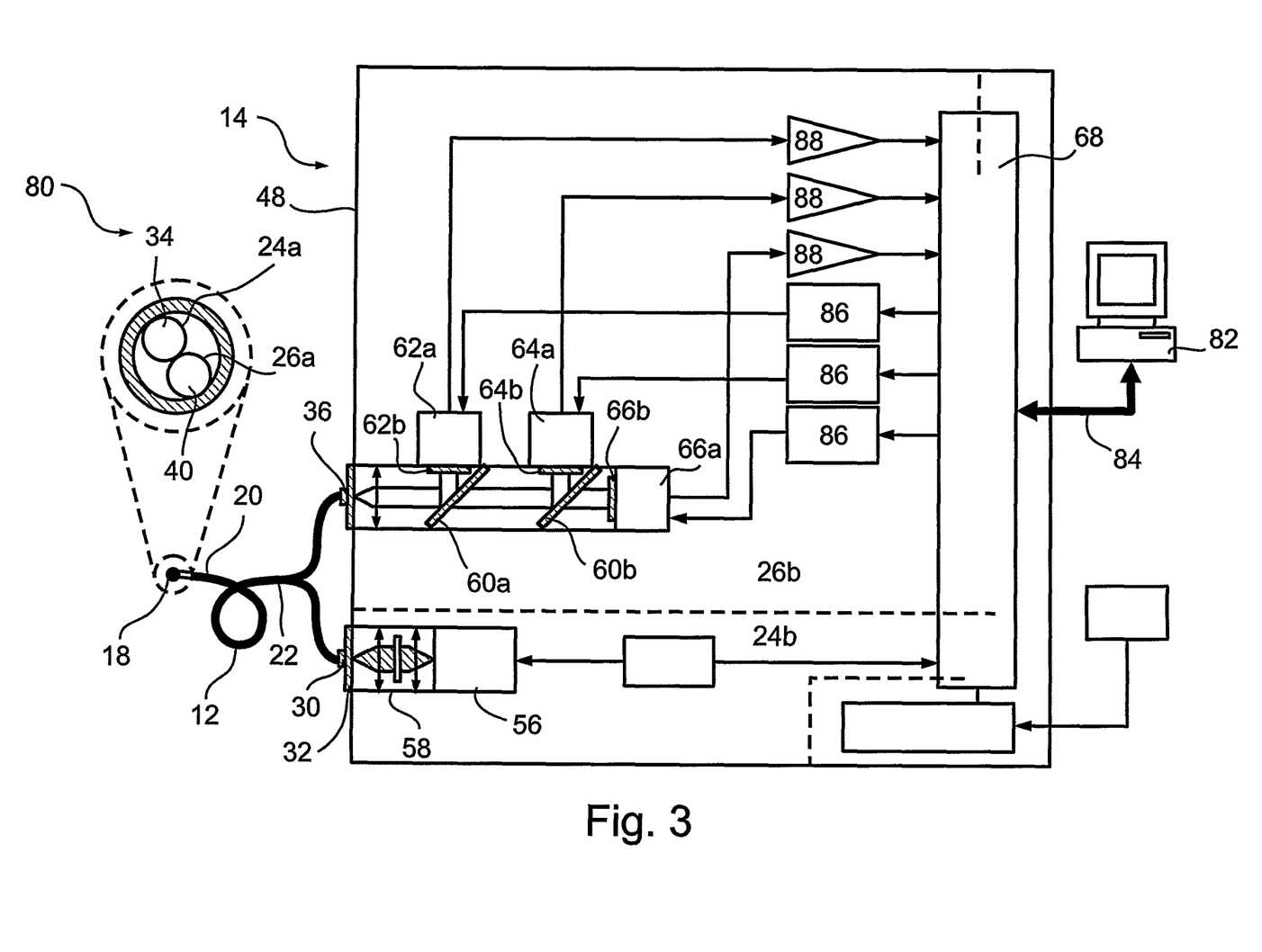
FIG. 3 is a schematic depiction of an embodiment of a device of the present invention.

An additional embodiment of the present invention, device 80 is schematically depicted in FIG. 3.

Device 80, like device 10 discussed above, comprises two physically separate components: an elongated probe 12 including two light guides and a device body 14 including other components of device 80 within a casing 48. A proximal end 22 of probe 12 is configured to reversibly couple to device body 14, substantially as described above for device 10.

Probe 12 of device 80 is configured to be disposable. Before use, each probe 12 is sterile and packaged in a sterility preserving package. Two discrete light guides (substantially optical fibers) pass through probe 12: an excitation light guide 24a that is a component of an excitation light unit 24 and a detection light guide 26a that is a component of a detection unit 26.

A distal end 18 of probe 12 has a 0.75 mm outer diameter and is configured to pass into and through a cervix, and a distal tip 20 of probe 12 is configured to contact an outer surface of an amniotic sac. As a distal tip 34 of excitation light guide 24a is flush with distal tip 20 of probe 12, distal tip 34 of excitation light guide 24 is configured to contact an outer surface of an amniotic sac.

Proximal end 22 of probe 12 is bifurcated. Excitation light guide 24a (e.g., a 250 micrometer diameter polymer optical fiber) is functionally associated with other components 24b of excitation unit 24 contained within casing 48 through excitation probe coupling adaptor 30 at proximal end 22 of probe 12. Detection light guide 26a (e.g., a 250 micrometer diameter polymer optical fiber) is functionally associated with other components 26b of detection unit 26 contained within casing 48 through detection probe coupling adaptor 36 at proximal end 22 of probe 12.

Unlike device 10, casing 48 of device 80 does not contain an integral controller. Rather, many control and analysis functions are performed by an external computer 82 (a suitable commercially available computer) which is functionally associated with the components of device 10 through analog to digital converter 68 with a standard communication cable 84 (e.g., an USB cable).

Components 24b of excitation unit 24 contained within casing 48 include an excitation light source 56 (a light-emitting diode) configured to emit substantially monochromatic light having a wavelength of about 405 nm, a collimator 58 and an excitation body coupling adaptor 32.

Components 26b of detection unit 26 contained within casing 48 include two beam splitters 60a (570DRLP) and 60b (590DRLP), three detectors 62a, 64a and 66a (photomultiplier tubes) functionally associated with three filters 62b (FB560-10, allowing passage of light having a wavelength of about 560 nm), 64b (FB580-10, allowing passage of light having a wavelength of about 580 nm) and 66b (FB600-10, allowing passage of light having a wavelength of about 600 nm). Each of detectors 62a, 64a and 66a is functionally associated with computer 82 through analog to digital converter 68, gain controllers 86 and amplifiers 88. In such a way, detection unit 26 is configured to detect the intensity of light emitted at 560 nm (by detector 62a) and 600 nm (by detector 66a) both as reference values to determine whether or not the intensity of light detected at 580 nm (by detector 64a) is significant enough to be indicative of ZnCP.

Unlike device 10, casing 48 of device 80 does not contain an integral self-contained power supply. Rather, power is supplied from external sources, in the usual way.

Unlike device 10, device 80 does not include an imaging unit.

Excitation unit 24 is configured to produce collimated light including a wavelength of about 405 nm with excitation light source 56 and, through excitation light guide 24a and to guide the light past the cervix to illuminate in vivo amniotic fluid.

Detection unit 26 is configured to detect the intensity of light emitted from the amniotic fluid indicative of the presence of ZnCP by guiding emitted light from distal tip 40 of detection light guide 26a through detection light guide 26a to other components 26b of detection unit 26.

Use of device 80 is substantially similar to the use of device 10 as discussed above with reference to FIG. 2. Since device 80 is devoid of an imaging unit, distal end 18 of probe 12 is maneuvered through the cervix with guidance from an external imaging modality such as ultrasound or by touch. After detection of the emitted light, detection unit 26 reports the intensities of light emitted at 560, 580 and 600 nm to computer 82 where the values are analyzed to determine if the values indicate the presence of ZnCP and consequently meconium in the examined amniotic fluid. For example, in embodiments, analysis of the values is performed substantially as described above by determining whether $2 \times I_{580}/(I_{560}+I_{600})$ is greater than 1 indicating the presence of ZnCP.

Figure 4A:
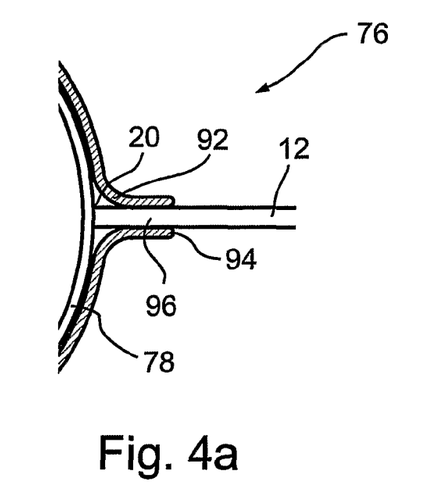
FIGS. 4a-4d depict embodiments where the distal tip of a probe of a device the present invention is located at different positions relative to the amniotic sac.

In embodiments discussed above, a distal tip 20 of a probe 12 including an excitation light guide 24 and a detection light guide 26a is passed entirely through a cervix 76 and placed against (contacts) the external wall of an amniotic sac 78 during the process of identifying the presence of meconium in the amniotic fluid, as depicted in FIG. 2 and FIG. 4A.

In some embodiments of the present invention, illumination with excitation light and/or detection of emitted light is performed without contacting the amniotic sac.

Figure 4B:
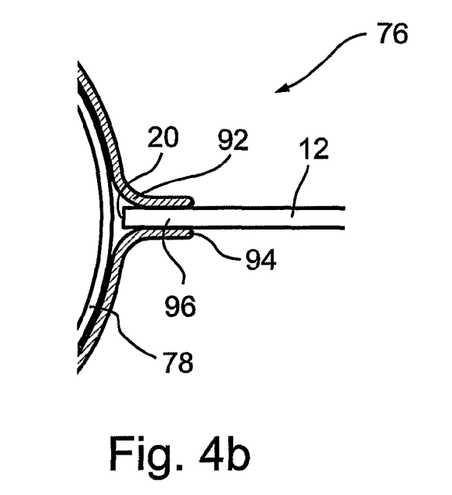

For example, in FIG. 4B is depicted an embodiment of the present invention where a distal tip 20 of a probe 12 including an excitation light guide 24 and a detection light guide 26a passes entirely through endocervical canal 90 (typically 2-3 cm long) so to emerge out through the internal os 92 of cervix 76 so that a detection unit functionally associated with detection light guide 26a detects the intensity of emitted light passing through a wall of amniotic sac 78 towards internal os 92 of endocervical canal 90.

Figure 4C:
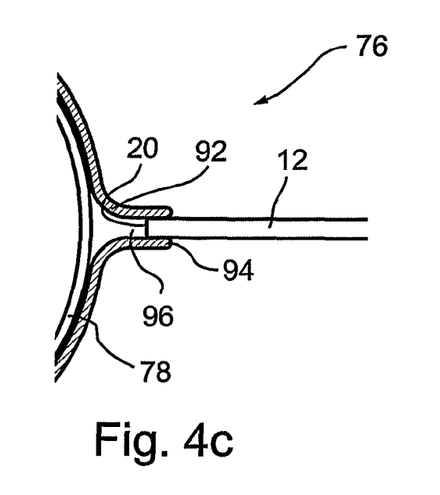

For example, in FIG. 4C is depicted an embodiment of the present invention where a distal tip 20 of a probe 12 including an excitation light guide 24 and a detection light guide 26a passes external os 94 into endocervical canal 90 of cervix 76 so that a detection unit functionally associated with detection light guide 26a detects the intensity of emitted light passing through a wall of amniotic sac 78 and entering, at least partially, the endocervical canal 90 of cervix 76.

Figure 4D:
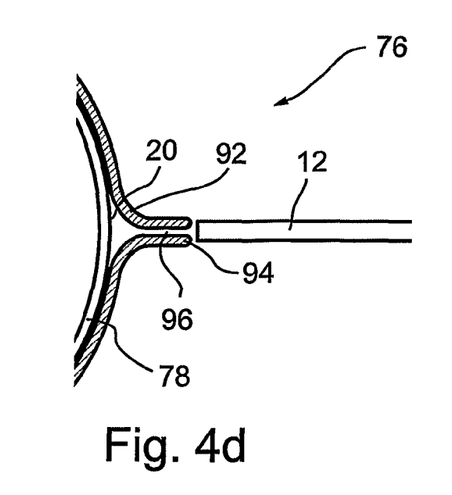

For example, in FIG. 4D is depicted an embodiment of the present invention where a distal tip 20 of a probe 12 including an excitation light guide 24 and a detection light guide 26a are placed proximal to the vaginal side of external os 94 so that a detection unit functionally associated with detection light guide 26a detects the intensity of emitted light passing through a wall of amniotic sac 78, passing through the mucosal plug in the endocervical canal (if present) and exiting out of endocervical canal 90 of cervix 76 through external os 94.

As noted above, one of the advantages of the teachings of the present invention is the potential high sensitivity of some embodiments of a device of the present invention resulting, in part, due to the fortuitous choice of excitation light that is absorbed by bodily tissue and that causes a fluorescent process that produces emitted light that that is also absorbed by bodily tissue.

Unexpectedly, it has been found that some embodiments of the present invention also allow the quantification of the amount of meconium in amniotic fluid. In the art it is known that the concentration of ZnCP in clear amniotic fluid is up to about 200 nmol liter$^{-1}$ and around 900 nmol liter$^{-1}$ in meconium-stained amniotic fluid. It has been found that for a given intensity of 405 nm excitation light, the intensity of light emitted by fluorescence $I_{580}$ upon excitation of amniotic fluid is linearly dependent on the concentration of ZnCP in the clinically relevant concentrations of up to about 1000 nmol/l, FIG. 5. When the intensity of emitted light is measured with the help of a light guide such as an optical fiber, the linear relationship is not influenced by the "depth" of amniotic fluid, apparently due to the fact that the aperture of an optical fiber is relatively small so that the emitted light is collected only from the volume of fluid that is close to the tip of the optical fiber. Thus, quantification of meconium in the amniotic fluid is not dependent on the position of the embryo, whether near to or far from a probe tip.

Figure 5:
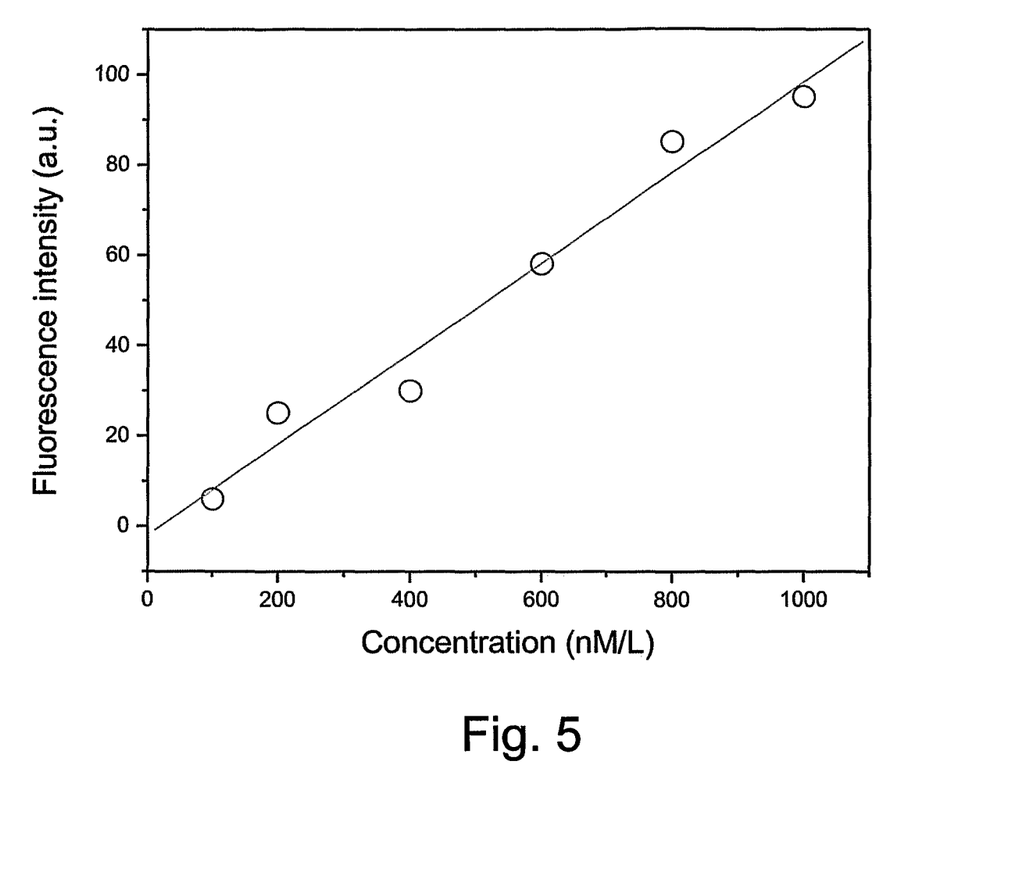
FIG. 5 is a graph showing the linear relationship between the intensity of light having a wavelength of 580 nm emitted by fluorescence of ZnCP excited by light having a wavelength of 405 nm in amniotic fluid and the concentration of the ZnCP.

In some embodiments, for example in some embodiments employing devices such as device 10 or device 80, when it is desired to quantify meconium in amniotic fluid in an amniotic sac, a probe (such as 12) to be used is functionally associated with a source of excitation light and with a detector. A calibration curve, for example such as depicted in FIG. 5, for the probe is generated, for example by measuring the intensity of light having a wavelength of 580 nm emitted by solutions (preferably at least two or even more solutions having different concentrations) of ZnCP in amniotic fluid at clinically relevant concentrations upon excitation with excitation light having a wavelength of 405 nm exiting the probe tip. A person having ordinary skill in the art is able to prepare appropriate solutions and use a device of the present invention to generate a suitable calibration curve upon perusal of the description herein and of the graph in FIG. 5.

In some embodiments, once the concentration of ZnCP in the meconium is quantified in accordance with the teachings of the present invention, the concentration of ZnCP quantified in the in vivo amniotic fluid is rated as a qualitative degree of meconium in the amniotic fluid, e.g. "clear" (up to about 200 nmol ZnCP liter$^{-1}$), "low" (between about 200 nmol ZnCP liter$^{-1}$ and 600 nmol ZnCP liter $^{-1}$), "medium" (between about 800 nmol ZnCP liter$^{-1}$ and 900 nmol ZnCP liter$^{-1}$) or "thick" (more than about 900 nmol ZnCP liter$^{-1}$).

EXPERIMENTAL

A device such as device 80 was made including sterilized and packaged intracervical probes. The irradiation power emitted from a probe distal tip was adjusted to be ~0.7 mW.

The amniotic fluids of 43 pregnant women having intact amniotic membrane were examined (qualitatively rather than quantitatively) substantially as described above. In eight cases the device qualitatively identified meconium in the amniotic fluid and in all other (35) cases the device did not identify meconium in the blood.

The results in five cases where the device qualitatively identified meconium in the amniotic fluid and in the 35 cases where the device did not identify meconium in the amniotic fluid were confirmed as correct, post partum, by an obstetrician demonstrating 100% sensitivity.

In three "false-positive" cases, the device identified meconium in the amniotic fluid but no meconium was observed by the obstetrician.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A device useful for in vivo identification of the presence of zinc-coproporphyrin I (ZnCP) in amniotic fluid, comprising:
    a) an excitation unit comprising a light source that, when turned on, produces an excitation light including a wavelength of about 405 nm,
    b) a detection unit capable of detecting an intensity of light emitted from in vivo amniotic fluid indicative of the presence of ZnCP, said indicative emitted light including a wavelength of about 580 nm, and c) at least one elongated probe having a distal end and a proximal end, said probe comprising an excitation light guide capable of guiding said excitation light from said light source out through the distal end of said probe and thereby causing the excitation light to pass through the wall of an amniotic sac and thereby illuminate the amniotic fluid in vivo, the distal end of said probe being so dimensioned as to pass into or through an endocervical canal, and d) a processor configured to correlate said intensity with the concentration of ZnCP in said amniotic fluid.

2. The device of claim 1, wherein said light source, when turned on, produces an excitation light that consists essentially of monochromatic light of about 405 nm.

3. The device of claim 1, wherein the diameter of said distal end of said elongated probe is no more than about 6 mm (18 French).

4. The device of claim 1, said probe including a detection light guide component of said detection unit configured to guide light from a distal tip of said probe to a light detector component of said detection unit.

5. The device of claim 4, wherein said detection light guide and said excitation light guide are discrete.

6. The device of claim 4, wherein said detection light guide and said excitation light guide are substantially the same.

7. The device of claim 1, comprising a device body containing said light source wherein a distal end of said probe is configured to reversibly couple to said device body so that when said probe is coupled to said device body, said probe is configured to direct excitation light through said excitation light guide and out through said distal end of said probe.

8. The device of claim 7, at least one said probe is sterile and packaged in a sterility preserving package.

9. The device of claim 1, wherein the diameter of said distal end of said elongated probe is no more than 4 mm (12 French).

10. The device of claim 1, wherein the diameter of said distal end of said elongated probe is no more than 3 mm (10 French).

11. The device of claim 1, wherein the diameter of said distal end of said elongated probe is no more than 2 mm (6 French).

12. The device of claim 1, wherein the diameter of said distal end of said elongated probe is no more than 1 mm (3 French).

13. The device of claim 1 wherein said probe comprises said light source.

14. The device of claim 1 wherein said light source is external to said probe.

15. A method for quantifying the concentration or identifying the presence of zinc-coproporphyrin I (ZnCP) in amniotic fluid, comprising:

a) providing an excitation unit configured to provide excitation light including a wavelength of about 405 nm;

b) inserting into or through the endocervical canal at least an excitation light-emitting portion of an elongated probe, said probe comprising an excitation light guide guiding said excitation light from said excitation unit out through said portion;

c) illuminating amniotic fluid through the wall of an amniotic sac with said excitation light including a wavelength of about 405 nm in order to excite ZnCP present in said amniotic fluid; and d) monitoring said illuminated amniotic fluid for emission of light indicative of the presence of ZnCP, said monitored indicative light comprising a wavelength of about 580 nm; quantifying the intensity of such light and correlating said intensity with the concentration of ZnCP in said amniotic fluid.

16. The method of any of claim 15, wherein said excitation light consists essentially of monochromatic light of about 405 nm.

17. The method of claim 15, wherein said monitoring of emission of light indicative of the presence of ZnCP comprises comparing a detected intensity of light of about 580 nm ($I_{580}$) with the intensity of light comprising wavelengths significantly shorter ($I_{short}$) and/or significantly longer ($I_{long}$) than 580 nm.

18. A method for identifying the presence of meconium in amniotic fluid which comprises measuring the concentration of ZnCP in said amniotic fluid by the method of claim 15 and correlating said concentration with the presence or absence of meconium therein.

19. The method of claim 15, wherein the diameter of said distal end of said elongated probe is no more than about 6 mm (18 French).

* * * * *